(12) United States Patent
Park et al.

(10) Patent No.: US 10,367,211 B2
(45) Date of Patent: Jul. 30, 2019

(54) METHOD FOR MANAGING ION FILTER OF FUEL CELL VEHICLE

(71) Applicant: HYUNDAI MOTOR COMPANY, Seoul (KR)

(72) Inventors: Hunwoo Park, Namyangju-si (KR); Sung Wook Na, Yongin-si (KR)

(73) Assignee: HYUNDAI MOTOR COMPANY, Seoul (KR)

( * ) Notice: Subject to any disclaimer, the term of this patent is extended or adjusted under 35 U.S.C. 154(b) by 364 days.

(21) Appl. No.: 15/077,651

(22) Filed: Mar. 22, 2016

(65) Prior Publication Data
US 2017/0104229 A1 Apr. 13, 2017

(30) Foreign Application Priority Data
Oct. 12, 2015 (KR) ........................ 10-2015-0142404

(51) Int. Cl.
| | | |
|---|---|---|
| G01M 3/32 | (2006.01) |
| H01M 8/0438 | (2016.01) |
| G01M 3/26 | (2006.01) |
| G01N 15/08 | (2006.01) |
| H01M 8/04992 | (2016.01) |
| H01M 8/04029 | (2016.01) |
| H01M 8/04044 | (2016.01) |
| H01M 8/04664 | (2016.01) |

(52) U.S. Cl.
CPC ......... *H01M 8/04417* (2013.01); *G01M 3/26* (2013.01); *G01M 3/3263* (2013.01); *G01N 15/0826* (2013.01); *H01M 8/04029* (2013.01); *H01M 8/04044* (2013.01); *H01M 8/04686* (2013.01); *H01M 8/04992* (2013.01); *G01N 2015/084* (2013.01); *H01M 2250/20* (2013.01); *Y02T 90/32* (2013.01)

(58) Field of Classification Search
CPC . H01M 8/04417; H01M 8/04432; G01M 3/26
USPC .................................................. 702/50; 73/40
See application file for complete search history.

(56) References Cited

U.S. PATENT DOCUMENTS

| 8,518,254 B2* | 8/2013 | Na ................. H01M 8/04044 210/282 |
| 2003/0141200 A1* | 7/2003 | Harada ................ C25B 1/12 205/637 |
| 2005/0058868 A1* | 3/2005 | Taga ................ H01M 8/04007 429/434 |
| 2005/0106433 A1* | 5/2005 | Takemoto ......... H01M 8/04029 210/167.32 |

(Continued)

FOREIGN PATENT DOCUMENTS

| JP | 2006-179332 A | 7/2006 |
| JP | 2006-316734 A | 11/2006 |

(Continued)

*Primary Examiner* — Son T Le
*Assistant Examiner* — Alexander A Mercado
(74) *Attorney, Agent, or Firm* — Morgan Lewis & Bockius LLP

(57) ABSTRACT

A method for managing an ion filter of a fuel cell vehicle includes measuring a differential pressure between ends of the ion filter, calculating a change of the differential pressure according to a coolant flow at the ion filter, and determining leakage of an ion resin or a replacement time of a cartridge using the measured differential pressure or the calculated change of the differential pressure.

7 Claims, 8 Drawing Sheets

(56) References Cited

U.S. PATENT DOCUMENTS

| | | | | |
|---|---|---|---|---|
| 2005/0260463 A1* | 11/2005 | Chapman | .......... | H01M 8/04179 |
| | | | | 429/432 |
| 2008/0113252 A1* | 5/2008 | Yamamoto | ........ | H01M 8/04097 |
| | | | | 429/415 |
| 2010/0068565 A1* | 3/2010 | Yadha | .................. | H01M 8/028 |
| | | | | 429/410 |
| 2011/0256470 A1* | 10/2011 | Na | .................... | H01M 8/04007 |
| | | | | 429/512 |
| 2013/0295478 A1* | 11/2013 | Han | ................. | H01M 8/04417 |
| | | | | 429/428 |
| 2014/0220468 A1* | 8/2014 | Lang | ................ | H01M 8/04029 |
| | | | | 429/436 |
| 2014/0248550 A1* | 9/2014 | Takemoto | ................ | C02F 1/42 |
| | | | | 429/434 |
| 2015/0004503 A1* | 1/2015 | Yamamoto | ........ | H01M 8/04104 |
| | | | | 429/410 |
| 2016/0351923 A1* | 12/2016 | Na | .................... | H01M 8/04044 |
| 2017/0030245 A1* | 2/2017 | Bokelund | ............. | F01N 11/002 |
| 2017/0104229 A1* | 4/2017 | Park | .................... | G01M 3/3263 |

FOREIGN PATENT DOCUMENTS

| | | |
|---|---|---|
| KR | 10-0957364 B1 | 5/2010 |
| KR | 10-2011-0061731 A | 6/2011 |
| KR | 10-1428413 B1 | 8/2014 |
| KR | 10-1509681 B1 | 4/2015 |

* cited by examiner

Ion resin 100%

Ion resin 80%

Ion resin 60%

METHOD FOR MANAGING ION FILTER OF FUEL CELL VEHICLE

CROSS-REFERENCE TO RELATED APPLICATION

This application claims the benefit of priority to Korean Patent Application No. 10-2015-0142404, filed with the Korean Intellectual Property Office on Oct. 12, 2015, the entire contents of which are incorporated herein by reference.

TECHNICAL FIELD

The present disclosure relates to a method for managing an ion filter of a fuel cell vehicle.

BACKGROUND

In general, a fuel cell system supplies hydrogen as a fuel and air as an oxidant to a fuel cell stack, and produces electricity through an electrochemical reaction between hydrogen and oxygen. The fuel cell system can be mounted in a vehicle, and can drive the vehicle by operating an electric motor with electricity produced by the fuel cell stack.

The fuel cell system refers to a type of electric power generation system which electrochemically converts chemical energy directly into electrical energy in the fuel cell stack.

Because a large amount of heat is generated in the fuel cell stack during a fuel cell reaction, a cooling apparatus is necessary to be provided in the fuel cell system in order to cool the system. Meanwhile, an antifreeze fluid is used in the fuel cell vehicle as a coolant.

The coolant may be injected in a pressurized manner after causing the cooling system to be in a vacuum state so that bubbles are not present in the cooling system.

If bubbles (air) are present in the cooling system when the coolant is injected, a possibility of overheating due to a coolant deficiency is increased. In a case in which the bubbles are present in the cooling system of the fuel cell vehicle, as described above, a deterioration in an efficiency of the fuel cell and cooling performance due to a local increase in temperature of the fuel cell stack can be caused, coolant flow noise can occur, and adverse conditions may result.

Therefore, the fuel cell vehicle includes an ion filter in order to remove bubbles that are present in the cooling system.

However, a replacement time of an ion filter cartridge is determined through volume change measured by a gauge mounted in the ion filter using a volume reduction principle of an ion resin.

Therefore, in the related art, it is difficult to determine the replacement time of the ion filter cartridge after opening an engine compartment of the vehicle and checking the gauge with the naked eye.

The above information disclosed in this Background section is only for enhancement of understanding of the background of the disclosure and therefore it may contain information that does not form the prior art that is already known in this country to a person of ordinary skill in the art.

SUMMARY OF THE DISCLOSURE

The present disclosure has been made in an effort to provide for managing an ion filter of a fuel cell vehicle having advantages of determining a leakage of an ion resin or a replacement time of a cartridge in the fuel cell vehicle.

An exemplary embodiment of the present disclosure provides a method for managing an ion filter of a fuel cell vehicle, the method including: measuring a differential pressure between ends of the ion filter; calculating a change of the differential pressure according to a coolant flow at the ion filter; and determining a leakage of an ion resin or a replacement time of a cartridge using the measured differential pressure or the calculated change of the differential pressure.

The step of measuring the differential pressure may include measuring a difference between a pressure of a coolant inflow end and a pressure of a coolant output end of the ion filter.

The step of determining may include determining whether the ion resin is leaked by comparing the change of the differential pressure with a predetermined decrease ratio of the differential pressure.

The predetermined decrease ratio of the differential pressure may include a change rate of the differential pressure by a volume reduction of the ion resin due to accumulation of driving time of the fuel cell vehicle.

The step of determining whether the ion resin is leaked may determine a leakage of the ion resin when the change of the differential pressure is greater than the predetermined decrease ratio of the differential pressure.

The method may further include setting a value of the differential pressure of mapping data according to an operation speed of a coolant pump and the coolant flow at the ion filter, before the measuring.

The step of setting may set the coolant flow at the ion filter according to the operation speed of the coolant pump, and set a size of the differential pressure of the ion filter according to the coolant flow at the ion filter.

The step of determining may include determining the leakage of the ion resin or the replacement time of the cartridge by comparing the measured differential pressure of the ion filter with the value of the differential pressure of to predetermined mapping data.

The predetermined mapping data may set the coolant flow or the size of the differential pressure according to a temperature of the coolant.

An exemplary embodiment of the present disclosure provides a method for determining ion resin leakage of an ion filter in fuel cell vehicle, the method including: measuring a differential pressure between ends of the ion filter; calculating a change of the differential pressure according to a coolant flow at the ion filter using the measured differential pressure; and determining whether the ion resin is leaked by comparing the change of the differential pressure with a predetermined decrease ratio of the differential pressure.

An exemplary embodiment of the present disclosure provides a method for determining cartridge replacement time of an ion filter in a fuel cell vehicle, the method including: setting a value of a differential pressure as mapping data according to an operation speed of a coolant pump and a coolant flow at the ion filter; measuring a differential pressure at ends of the ion filter; and determining a replacement time of a cartridge by comparing the measured differential pressure of the ion filter with the value of the differential pressure of predetermined mapping data.

According to the present disclosure for achieving the object, by setting the coolant flow and the differential pressure of the ion filter according to the operation speed of the coolant pump in the fuel cell vehicle, measuring the differential pressure between both ends of the ion filter, and comparing the measured differential pressure with the change of the differential pressure and the predetermined mapping data, it is possible to notify the driver of the leakage of the ion resin and the replacement time of the cartridge.

DETAILED DESCRIPTION

Figure 1:
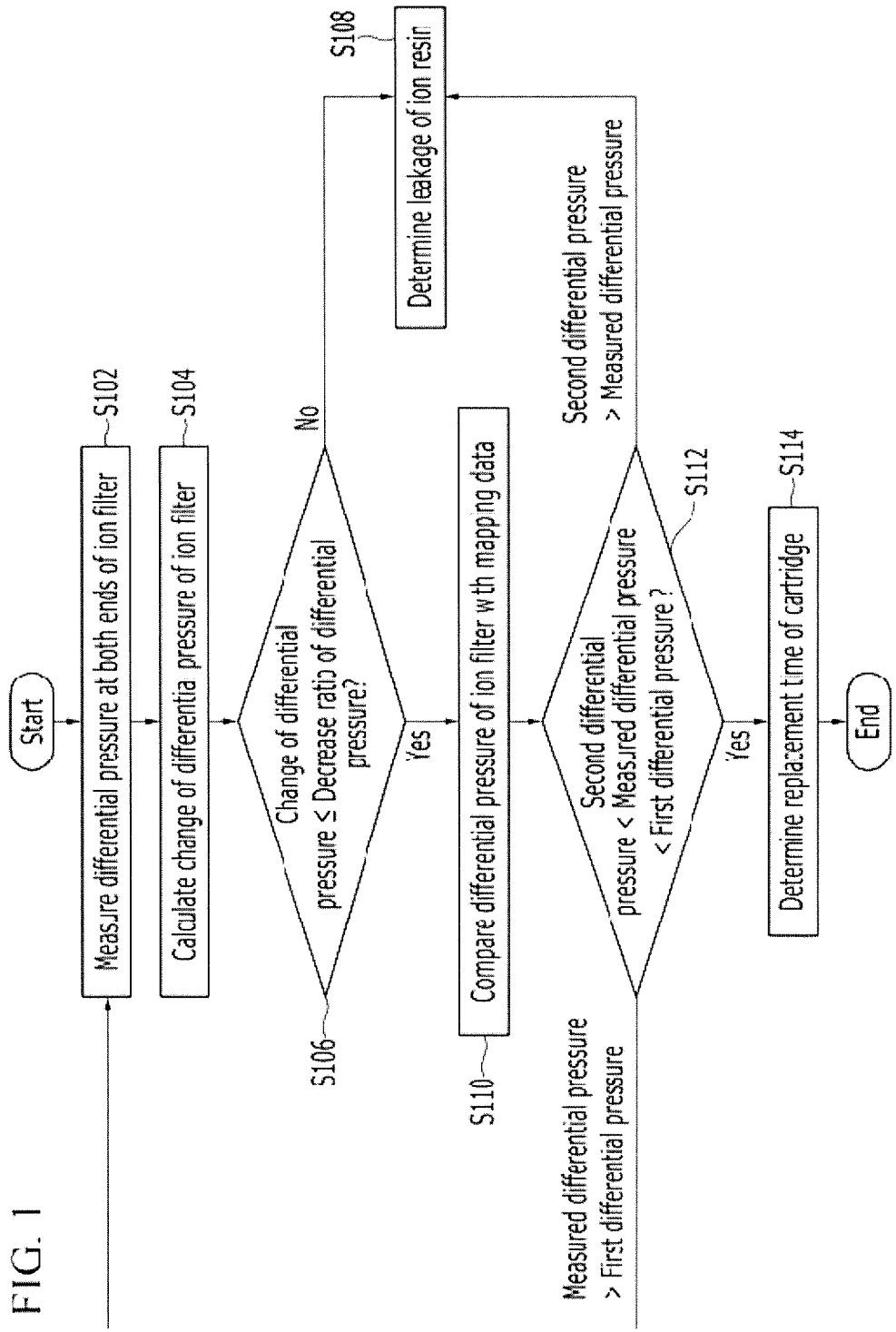
FIG. 1 is a flowchart showing a process for measuring a differential pressure of an ion filter in a fuel cell vehicle and determining leakage of an ion resin and a replacement time of a cartridge according to an exemplary embodiment of the present disclosure.

In the following detailed description, only certain exemplary embodiments of the present disclosure have been shown and described, simply by way of illustration. As those skilled in the art would realize, the described embodiments may be modified in various different ways, all without departing from the spirit or scope of the present disclosure.

Throughout the specification, unless explicitly described to the contrary, the word "comprise" and variations such as "comprises" or "comprising" will be understood to imply the inclusion of stated elements but not the exclusion of any other elements.

Parts indicated by like reference numerals are the same components throughout the specification.

It is understood that the term "vehicle" or "vehicular" or other similar terms as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles, and other alternative fuel vehicles (e.g., fuel derived from resources other than petroleum).

In addition, some methods may be executed by at least one controller. The term "controller" refers to a hardware device including a memory and a processor configured to execute one or more steps interpreted as an algorithm structure. The memory stores algorithm steps, and the processor specifically executes the algorithm steps to perform one or more processes to be described below.

Further, control logic of the present disclosure may be implemented by a non-transient computer-readable medium on a computer-readable means including executable program instructions executed by a processor, a controller, or the like. Examples of a computer-readable medium, although not restrictive, include ROMs, RAMs, CD-ROMs, magnetic tapes, floppy disks, flash drives, smart cards, and optical data storages. The computer-readable recording medium may be distributed in a network-connected computer system, and for example, may be stored and executed in a distributed manner by a telematics server or Controller Area Network (CAN).

A method for managing an ion filter of a fuel cell vehicle will now be described with reference to FIG. 1 to FIG. 6.

FIG. 1 is a flowchart showing a process for measuring a differential pressure of an ion filter in a fuel cell vehicle and determining leakage of an ion resin and a replacement time of a cartridge according to an exemplary embodiment of the present disclosure.

Referring to FIG. 1, a device for managing an ion filter (not shown) according to an exemplary embodiment of the present disclosure measures pressures at both ends of the ion filter at step S102. The device for managing the ion filter may determine leakage of an ion resin and a replacement time of a cartridge using a differential pressure of the ion filter in a cooling system.

The cooling system is applied to the fuel cell, which generates electrical energy through an electrochemical reaction between fuel and an oxidizer. The fuel cell vehicle may drive an electric motor with electrical energy produced by the electrochemical reaction between the fuel and the oxidant.

Figure 2:
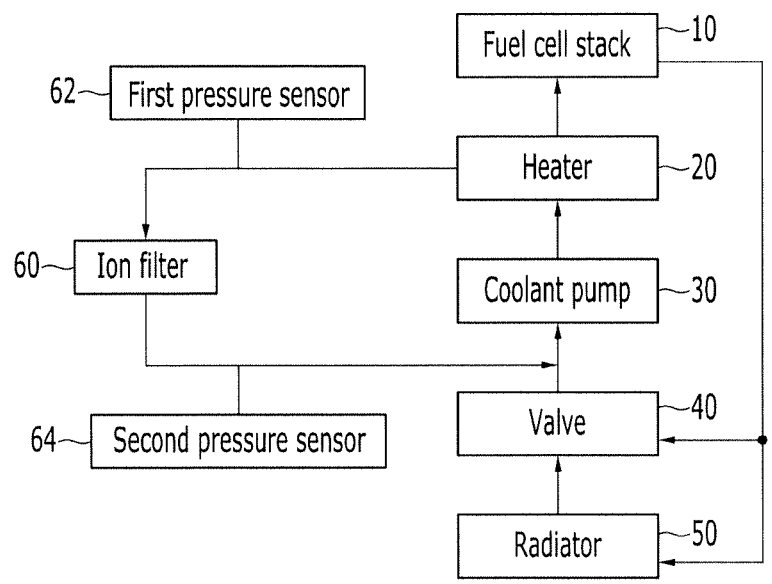
FIG. 2 is a schematic diagram of a cooling system of a fuel cell vehicle according to an exemplary embodiment of the present disclosure.

FIG. 2 is a schematic diagram of a cooling system of a fuel cell vehicle according to an exemplary embodiment of the present disclosure.

In this case, for convenience of explanation, a configuration of the cooling system of the fuel cell vehicle according to an exemplary embodiment of the present disclosure is schematically illustrated, but the cooling system is not limited thereto.

Referring to FIG. 2, the cooling system of the fuel cell vehicle may include a fuel cell stack 10, a heater 20, a coolant pump 30, a valve 40, a radiator 50 and an ion filter 60.

Because a large amount of heat is generated in the fuel cell stack 10 during a fuel cell reaction, a cooling apparatus is necessary to be provided in the fuel cell system in order to cool the system. The cooling system of the fuel cell vehicle includes the ion filter 60 to remove bubbles that may be present in the cooling system.

The coolant that passes through the coolant pump 30 may be supplied to the fuel cell stack 10 through the heater 20. The coolant that passes through the fuel cell stack 10 flows into the coolant pump 30 through the valve 40 or the radiator 50. A predetermined amount of the coolant flows into the ion filter 60 from the heater 20, and a coolant flow that flows into the ion filter 60 may be determined according to an operation speed of the coolant pump 30.

A device for managing the ion filter according to an exemplary embodiment of the present disclosure may measure a differential pressure of the ion filter 60 by using a first pressure sensor 62 and a second pressure sensor 64 disposed at respective ends of the ion filter 60. The differential pressure of the ion filter 60 is a difference between a pressure of a coolant inflow end and a pressure of a coolant output end of the ion filter.

The device for managing the ion filter according to an exemplary embodiment of the present disclosure calculates a change of the differential pressure of the ion filter, and compares the change of the differential pressure with a predetermined decrease ratio of the differential pressure at step S104 and S106.

In this case, when the change of the differential pressure is smaller than the predetermined decrease ratio of the differential pressure, it may be determined that the ion filter is in a normal state, and when the change of the differential pressure is greater than the predetermined decrease ratio of the differential pressure, it may be determined that the ion resin leaks at step S108. Herein, the predetermined decrease ratio of the differential pressure may include a change rate of the differential pressure by a normal volume reduction of the ion resin due to accumulation of operation time of the fuel cell vehicle.

A device for managing the ion filter according to an exemplary embodiment of the present disclosure determines a replacement time of a cartridge and leakage of the ion resin by comparing the differential pressure of the ion filter with predetermined mapping data at step S110.

Herein, a device for managing the ion filter according to an exemplary embodiment of the present disclosure can set a value of the differential pressure of the ion filter due to an operation speed of the coolant pump and coolant flow. The coolant flow at the ion filter according to the operation speed of the coolant pump may be determined by the predetermined mapping data, and the differential pressure according to the coolant flow at the ion filter may be determined in the predetermined mapping data.

Figure 3:
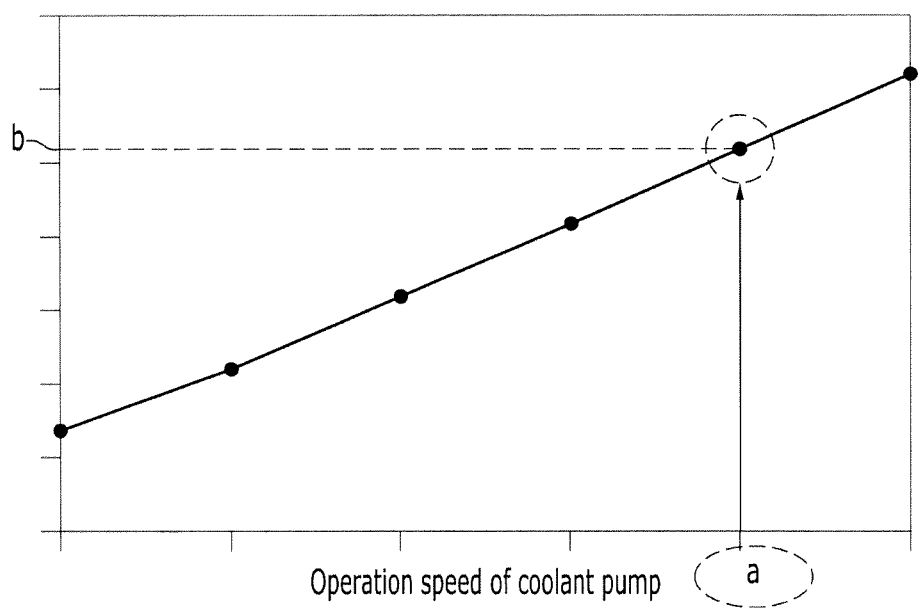
FIG. 3 is a graph showing a coolant flow at an ion filter according to an operation speed of a coolant pump according to an exemplary embodiment of the present disclosure.
Figure 4A:
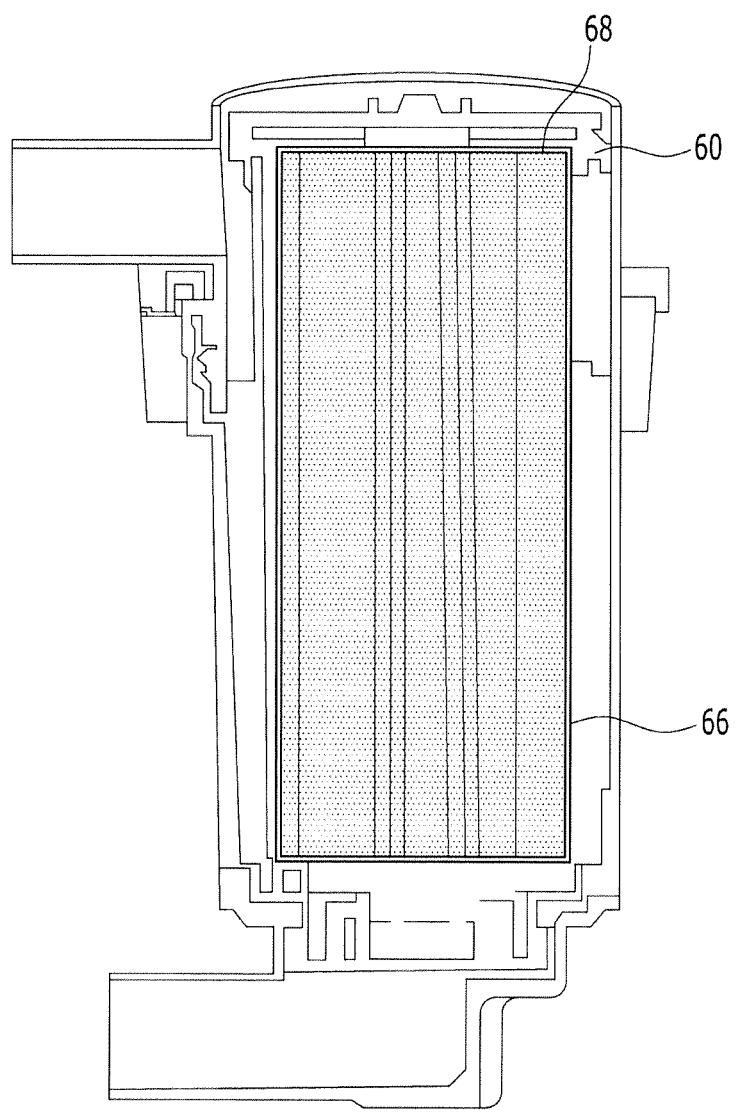
FIG. 4A, FIG. 4B, and FIG. 4C are drawings respectively showing an ion resin filled to 100%, 80% and 60%.
Figure 4B:
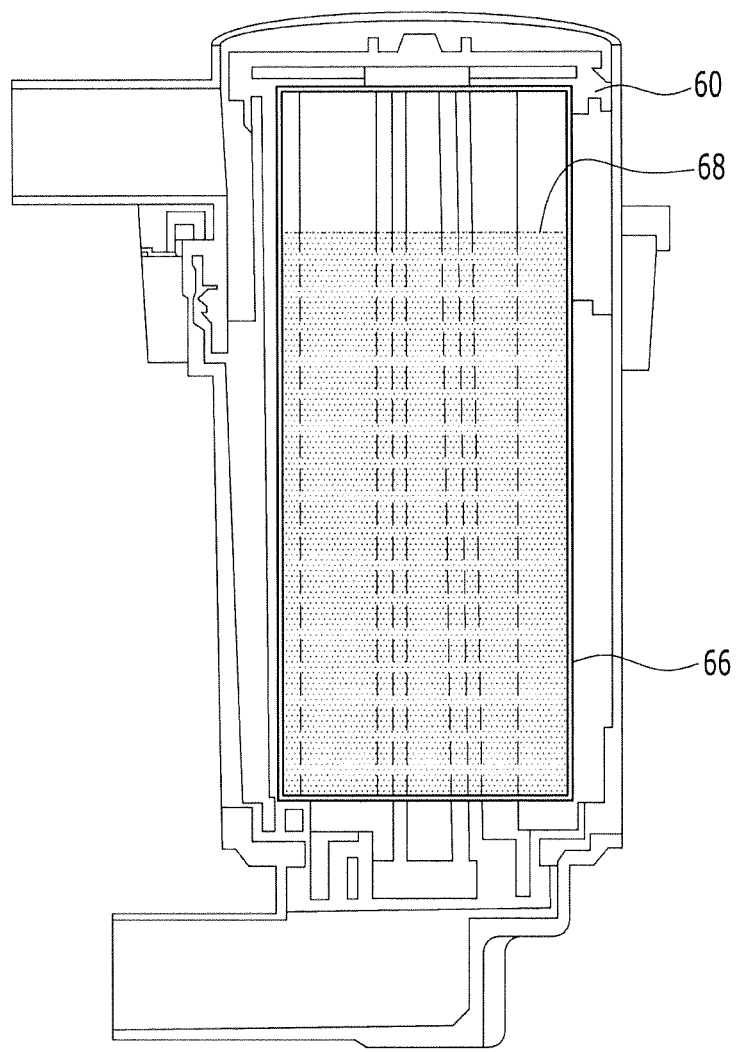
Figure 4C:
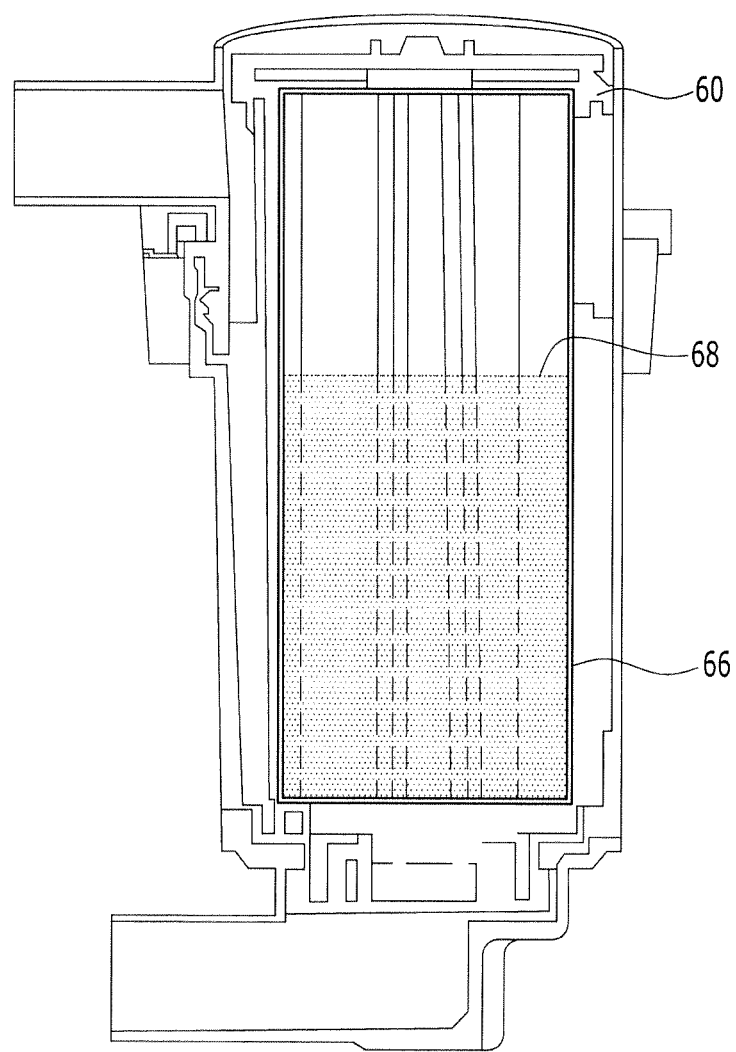
Figure 5:
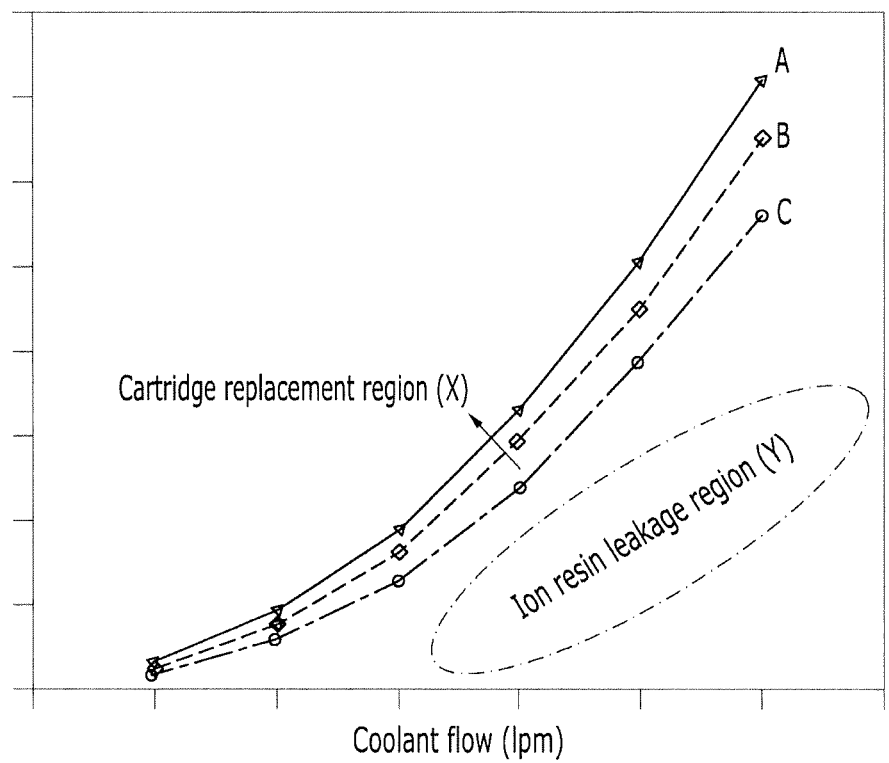
FIG. 5 is a graph showing a differential pressure of an ion filter according to a coolant flow at the ion filter of FIG. 3.

FIG. 3 is a graph showing a coolant flow at an ion filter according to an operation speed of a coolant pump according to an exemplary embodiment of the present disclosure, FIG. 4A, FIG. 4B and FIG. 4C are drawings respectively showing ion resin filled to 100%, 80% and 60%, and FIG. 5 is a graph showing a differential pressure of an ion filter according to a coolant flow at the ion filter of FIG. 3.

Referring to FIG. 3, the device for managing the ion filter according to an exemplary embodiment of the present disclosure determines the coolant flow B passing the ion filter according to the operation speed A of the coolant pump. The device for managing the ion filter maps the differential pressure according to the coolant flow at the ion filter. Herein, a size of the differential pressure due to the coolant flow at the ion filter can be determined according to a volume of the ion resin.

Referring to FIG. 5, a curve A shows the differential pressure according to the coolant flow at the ion filter when the ion resin 68 is filled to 100% in a cartridge 66 as shown in FIG. 4A. A curve B shows the differential pressure according to the coolant flow at the ion filter when the ion resin 68 of the ion filter is filled to 80% in the cartridge 66 as shown in FIG. 4B, and the device for managing the ion filter may determine a replacement time of a cartridge by using the curve B. Curve C shows leakage of the ion resin when the ion resin 68 of the ion filter is filled to 60% in the cartridge 66 as shown in FIG. 4C. Herein, volume of the ion resin may be variously modified according to an environment of the cooling system according to an exemplary embodiment of the present disclosure.

Figure 6:
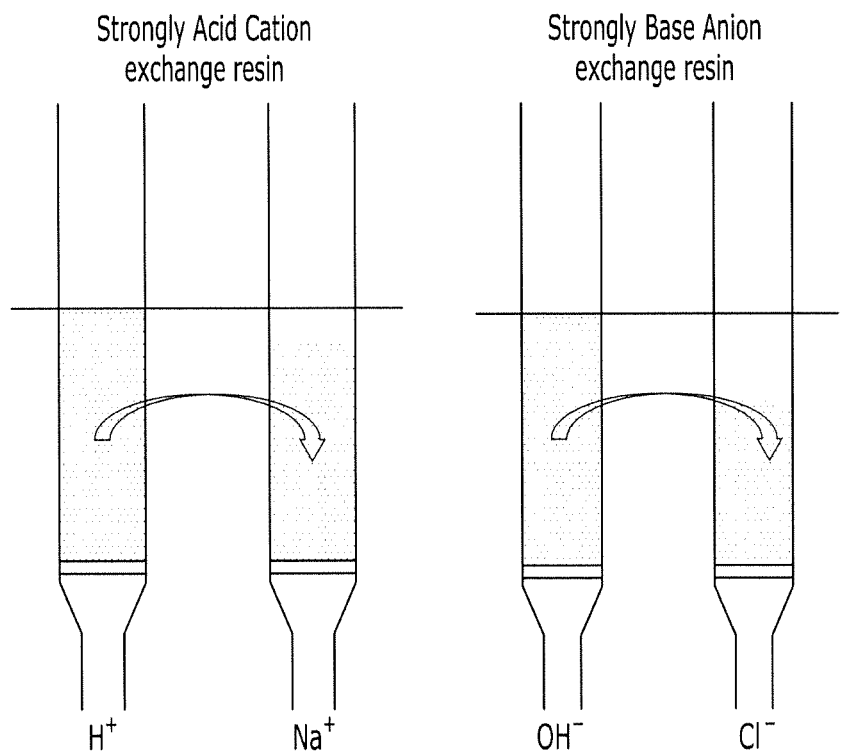
FIG. 6 is a drawing showing a volume reduction principle of an ion resin according to a type of ion resin.

FIG. 6 is a drawing showing a volume reduction principle of an ion resin according to a type of ion resin. The volume of the ion resin may be determined according to the type of the ion resin.

Referring to FIG. 6, when the ion resin is a Strongly Acid Cation (SAC) exchange resin, the replacement time of the cartridge can be set for when the volume of the ion resin is reduced by about 8%. Further, when the ion resin is a Strongly Base Anion (SBA) exchange resin, the replacement time of the cartridge can be set for when the volume of the ion resin is reduced by about 22%.

In addition, the coolant flow at the ion filter according to the operation speed of the coolant pump or the differential pressure according to the coolant flow at the ion filter may be differently set according to a temperature of the coolant. Since viscosity changes according to a temperature of the coolant, the differential pressure may be reduced by a temperature rise of the coolant.

As shown in FIG. 5, a device for managing the ion filter according to an exemplary embodiment of the present disclosure can set a cartridge replacement region X and an ion resin leakage region Y according to the differential pressure due to the coolant flow at the ion filter.

A device for managing the ion filter according to an exemplary embodiment of the present disclosure may determine the replacement time of the cartridge or the leakage of the ion resin by comparing the measured differential pressure with a first differential pressure according to the curve B and a second differential pressure according to the curve C in FIG. 4 at steps S112 and S114.

For example, when the measured differential pressure between both ends of the ion filter is greater than the second differential pressure according to the curve C and lower than the first differential pressure according to the curve B, it may be determined to be in the cartridge replacement region X. In this case, the device for managing the ion filter according to an exemplary embodiment of the present disclosure can determine the replacement time of the cartridge, and notify a driver thereof through a cartridge replacement signal.

In addition, when the measured differential pressure is lower than the second differential pressure according to the curve C, the device for managing the ion filter determines it to be in the ion resin leakage region Y, and warns the driver of the leakage of the ion resin. In this case, if the replacement time of the cartridge or the leakage of the ion resin is determined, the device for managing the ion filter according to an exemplary embodiment of the present disclosure may warn the driver by using a warning lamp on a cluster.

To this end, the device for managing the ion filter of the fuel cell vehicle according to an exemplary embodiment of the present disclosure may be realized by one or more processors activated by a predetermined program, and the predetermined program may be programmed to perform each step of a method for managing the ion filter according to an exemplary embodiment of the present disclosure.

As described above, the method for managing the ion filter of the fuel cell vehicle according to an exemplary embodiment of the present disclosure sets the coolant flow and the differential pressure of the ion filter according to an operation speed of the coolant pump in the fuel cell vehicle, measures the differential pressure between both ends of the ion filter, and compares the measured differential pressure with the change of the differential pressure and the predetermined mapping data. Therefore, it is possible to notify the driver of the leakage of the ion resin and the replacement time of the cartridge.

The foregoing exemplary embodiments of the present disclosure are not implemented only by an apparatus and a method, and may be realized by programs realizing functions corresponding to the configuration of the exemplary embodiment of the present disclosure or recording media on which the programs are recorded. Such recording media may be executed in a user terminal as well as a server.

While this disclosure has been described in connection with what is presently considered to be practical exemplary embodiments, it is to be understood that the disclosure is not limited to the disclosed embodiments, but, on the contrary, is intended to cover various modifications and equivalent arrangements included within the spirit and scope of the appended claims.

What is claimed is:

1. A method for monitoring an ion filter of a fuel cell vehicle, the method comprising steps of:

measuring a differential pressure between ends of the ion filter by using pressure sensors disposed at respective ends of the ion filter;

calculating a change of the differential pressure according to a coolant flow at the ion filter; and determining leakage of an ion resin of the ion filter or a replacement time of a cartridge having the ion resin therein using the differential pressure or the change of the differential pressure, wherein the step of measuring the differential pressure includes measuring a difference between a pressure of a coolant inflow end and a pressure of a coolant output end of the ion filter, wherein the step of determining includes:
    determining whether the ion resin is leaked by comparing the change of the differential pressure with a predetermined decrease ratio of the differential pressure; and
    determining the replacement time by comparing the differential pressure with a differential pressure according to predetermined mapping data of an operation speed of a coolant pump and the coolant flow at the ion filter, and wherein the method further comprises a step of, before the step of measuring the differential pressure, setting a value of the differential pressure according to the predetermined mapping data.

2. The method of claim 1, wherein the predetermined decrease ratio of the differential pressure includes a change rate of the differential pressure by a volume reduction of the ion resin due to accumulation of driving time of the fuel cell vehicle.

3. The method of claim 2, wherein the step of determining whether the ion resin is leaked determines a leakage of the ion resin when the change of the differential pressure is greater than the predetermined decrease ratio of the differential pressure.

4. The method of claim 1, wherein the step of setting sets the coolant flow at the ion filter according to the operation speed of the coolant pump, and sets a size of the differential pressure of the ion filter according to the coolant flow at the ion filter.

5. The method of claim 4, wherein the predetermined mapping data is set for the coolant flow or the size of the differential pressure according to a temperature of the coolant.

6. The method of claim 1, further comprising:
    warning, by a warning lamp, a user of the leakage when, it is determined that the differential pressure or the change of the differential pressure is equal to or over a first reference or warning the user that the cartridge needs to be replaced when it is determined that the differential pressure or the change of the differential pressure is equal to or over a second reference.

7. A method for determining cartridge replacement time of an ion filter in a fuel cell vehicle, the method comprising:
    setting a value of a differential pressure according to predetermined mapping data of an operation speed of a coolant pump and a coolant flow at the ion filter;
    measuring a differential pressure at ends of the ion filter; and
    determining a replacement time of a cartridge by comparing the measured differential pressure of the ion filter with the value of the differential pressure according to the predetermined mapping data.

* * * * *